United States Patent [19]
Komatsu et al.

[11] 3,987,166
[45] Oct. 19, 1976

[54] TREATMENT OF TUMORS WITH GLUCAN COMPOSITIONS IN MICE AND RATS

[75] Inventors: Nobuhiko Komatsu; Sumio Sakai; Gosaku Saito; Syoichi Kikumoto; Keitaro Kimura, all of Tokyo, Japan

[73] Assignees: Kaken Kagaku Kabushiki Kaisha; Taito Co., Ltd., both of Japan

[22] Filed: May 22, 1972

[21] Appl. No.: 255,682

Related U.S. Application Data

[63] Continuation of Ser. No. 37,029, May 13, 1970, abandoned, which is a continuation-in-part of Ser. No. 766,630, Oct. 10, 1968, abandoned.

[52] U.S. Cl. .............................. 424/180; 424/209; 424/274; 424/325

[51] Int. Cl.² ........................................ A61K 31/70
[58] Field of Search .......... 424/180, 209, 274, 325; 260/209

[56]  References Cited
UNITED STATES PATENTS
3,301,848   1/1967   Halleck .............................. 260/209

Primary Examiner—Jerome D. Goldberg
Attorney, Agent, or Firm—Bucknam and Archer

[57] ABSTRACT

A treatment of malignant tumors by administration of therapeutic compositions comprising the chemical compound "glucan".

7 Claims, No Drawings

TREATMENT OF TUMORS WITH GLUCAN COMPOSITIONS IN MICE AND RATS

This application is a continuation of Ser. No. 37,029, filed May 13, 1970, which was a continuation-in-part of Ser. No. 766,630, filed Oct. 10, 1968. Ser. No. 766,630 and Ser. No. 37,029 have now been abandoned.

BRIEF SUMMARY OF THE INVENTION

The present invention relates to a method for treating malignant tumors in mice and rats, and to a composition comprising a glucan in the form of an aqueous solution, and a composition comprising a glucan and known antitumor and/or anticancer agents which is useful as a medicinal preparation for such treatment.

The glucans, the subject matter of the present invention, are polymers of linearly $\beta$-(1 → 3)-linked D-glucopyranose residues having side chains at various intervals thereon, each of said side chains comprising one mole of $\beta$-(1 → 6)-linked D-glucopyranose residue, the general structure of said glucans is shown as follows:

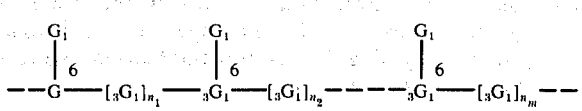

wherein G represents a $\beta$-D-glucopyranose residue, the indicia 1, 3 and 6 indicate the positions wherein adjacent glucose residues are linked, each [$_3G_1$] unit representing linearly $\beta$-(1 → 3)-linked D-glucopyranose residues, and each of $n_1 \ldots n_m$ being the number of said linearly linked glucose residues in each [$_3G_1$] unit, said $n_1 \ldots n_m$ being independently a number from 0 to about ten.

The general structure of the glucans is thus as follows, with the structure for each G being shown in conventional form and the numbering of one of the pyranose rings being indicated:

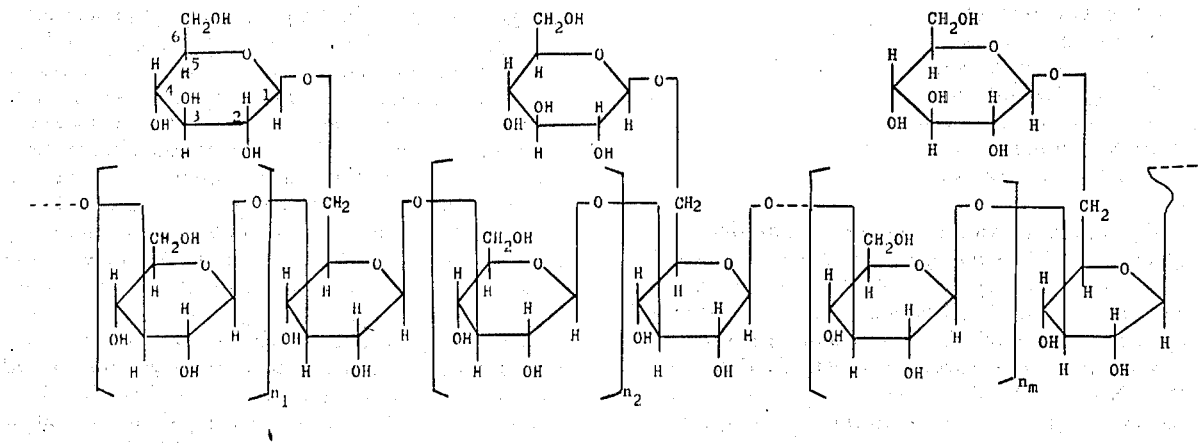

wherein $n_1, n_2, \text{------} n_m$ are defined above. For a better understanding, by way of example, a glucan in which all $n$ are 2 is shown a follows:

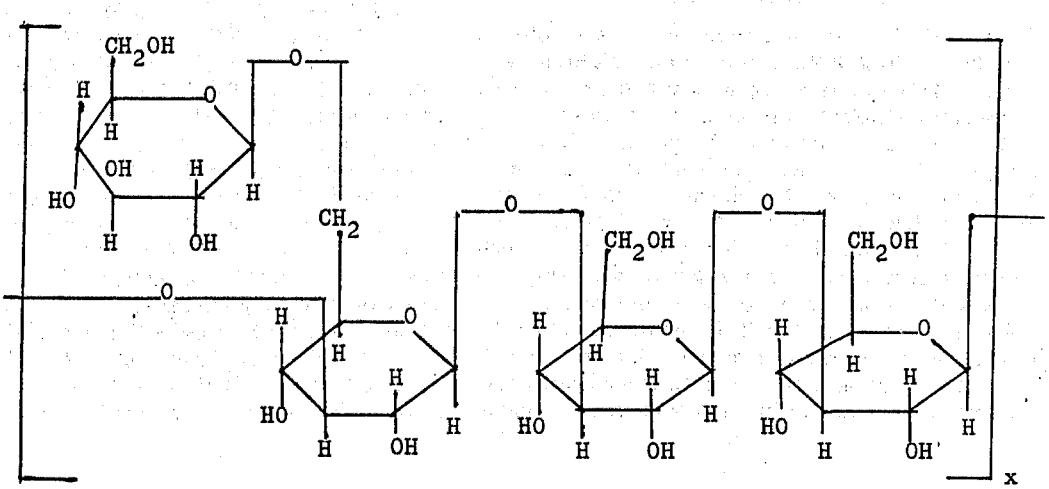

where x is more than 3.

As is known, glucans of the above formulas can be obtained from various fungi. It has now been found in our Laboratories that a large number of fungi belonging to the following strains also produce the glucans having an antitumor activity.

A. Ascomycetes:

Chaetomium cochliodes
Cochliobolus sativus
Ophiobolus miyabeanus
Pyrenophora teres
Sclerotinia arachidis
Sclerotinia mali
Sclerotinia sclerotiorum B. Basidiomycetes:

Corticium centrifugum
Flammulina velutipes
Lentinus edodes
Lindera bicolumnata
Melanoleuca verrucipes
Pholiota nameko
Russula emetica
Russula sororia
Scleroderma cepa C. Fungi imperfecti:

Alternaria kikutiana
Cercospora cryptomeriae
Cladosporium fulvum
Myrothecium verrucaria
Sclerotium tuliparum
Sclerotium hydrophylum The strains previously reported as producing such glucans are *Sclerotinia libertiana* (M. Kitahara et al.: *J. Agr. Chem. Soc. Japan*, 35, 468, 474 (1961)), *Sclerotium glucanicum, Sclerotium delphinii, Sclerotium rolfsii, Sclerotium coffeicolum, Corticium rolfsii, Sclerotinia gladoli*, and *Stromatinia narcissi* (F. E. Halleck: U.S. Pat. No. 3,301,848), *Schizophyllum commune* (S. Kikumoto et al.: *Taito Kenkyusho Hokoku*, 22, 77 (1964), 23, 77 (1965), Japanese Patent 505,408), *Claviceps purpurea* and *Claviceps fusiformis* (A. S. Perlin et al.: *Can. J. Chem.*, 41, 2278 – 82 (1963), and K. Buck et al.: *J. Gen. Microbiol.*, 51, 337 (1968)). Some of these glucans are useful as additives in the paper industry and as non-caloric stable gelling agents in the food industry.

DETAILED DESCRIPTION

According to the present invention it has been found that pharmaceutical preparations of these glucans and derivatives thereof have a significant antitumor action, with many complete remissions of the tumor. The mode of antitumor action of the glucans is different from that of the so-called cytotoxic anticancer agents such as Mitomycin-C (Merck Index, 8th Ed., April, 1968, P. 698, left column) and Nitromin (Merck Index, 8th Ed., April 1968, P. 647, left column), etc., which are now in common clinical use. For instance, a preparation of the present invention does not destroy tumor cells in in vitro contact test. This fact indicates that the preparation does not attack tumor cells directly, but, after administration, it stimulates certain internal organs of the mice and rats, which are believed to be the reticuloendothelial system such as the spleen, to produce an antitumor substance indirectly, resulting in a host-mediated antitumor action. This makes the glucans quite a unique preparation.

Another important advantageous feature of the glucans of the present invention is that they are non-toxic to a tumor-bearing mouse or rat by pathological observations in subacute toxicity in mice and rats. Although the above-mentioned cytotoxic anticancer agents damage not only tumor cells but also normal cells, the preparations of the present invention never injure normal cells because of their action through the above-mentioned mechanism. In acute toxicity tests by intraperitoneal injection of this glucan solution in mice, it was found that a continuous administration for 1 week in a dose of 100 mg/kg/day did not cause death. Administration of a larger amount of the preparation was not possible, since a higher concentration of the glucan tended to form viscous gel and could not be dissolved homogeneously.

Decrease in leucocytes, one of the initial side effects of cytotoxic anticancer agents, was not observed. In general, it is known that cytotoxic and antagonistic anticancer agents repress the functions of reticuloendothelial system, resulting in lowered resistance of the host against tumors, and rapid growth of tumors causes death of the tumor-bearing host. These facts considerably decrease the utility of the current anticancer agents. By contrast, the preparation of the present invention stimulates the functions of the reticuloendothelial system, so that it is possible to use it in combination with the current anticancer agents now being employed clinically, which allows a dosage of larger amounts of anticancer agents in total. Therefore, the present preparation has an important advantage that a sufficient dose can be given to obtain therapeutic effect. In this connection, various tests on rats given 1, 5 or 25 mg/kg of the glucan of the present invention once daily intraperitoneally for one or three months showed no abnormality in the increase of body weight, blood picture, various biochemical examinations, weight of internal organs, and histopathological findings, except for an increase of γ-globulin in serum, which is not an ill effect, and a splenomegaly observed only in a group given a dosage as high as 25 mg/kg. The present preparations are different from the polysaccharides isolated from certain bacteria. Such bacterial polysaccharides are known to induce hemorrhagic destruction of tumors and to be pyrogenic to animals.

The tumors employed in the tests are sarcoma-37, sarcoma-180, and Ehrlich carcinoma in mice, and Yoshida sarcoma in rats, all in solid form. Growth of the tumor was observed for one month. The present preparations showed a significant inhibitory effect against the growth of all tumors tested in doses of 0.1 – 10 mg/kg/day, preferably 0.25 – 5 mg/kg/day, presenting an inhibition ratio of more than 80%, being accompanied with many complete remissions of tumors.

The above results are superior to those obtained with Mitomycin C and Nitromin when compared by the same experimental procedures. In these tests, the optimal intraperitoneal doses of Mitomycin C and Nitromin are 1.8 mg/kg/day and 10 mg/kg/day, respectively, and a dose twice that amount always causes death of the test animals. On the other hand, the present preparation does not kill the mice and rats even in a dosage as high as 100 mg/kg/day, and shows a therapeutic effect in a dose as low as 0.14 mg/kg. Thus, it can be seen tha there is a great difference between therapeutically active dosages and dosages which are toxic. Even under severe experimental conditions wherein both Mitomycin C and Nitromin were ineffective, the present preparation was still effective.

The effective dosage for administration to tumor-bearing mice and rats is from about 0.1 to about 10 mg/kg/day. However, we do not wish to limit the dosage within these values since the dosage can vary substantially in individual cases. Moreover, it is very interesting and clinically useful that the antitumor activity is remarkably fortified in case where both glucan of the present invention and known anticancer agents such as Mitomycin, Eondoxan and Nitromin were employed than in the case where each reagent was solely employed, and in this case, toxicities of the known anticancer agents can be diminished remarkably.

The glucans of the present invention are dissolved in physiological saline and other physiologically tolerated vehicles such as Ringer's or aqueous glucose solution. The preparations are usually administered intravenously, intramuscularly, subcutaneously, or intraperitoneally into tumor-bearing mice and rats.

The glucans of the present invention can be obtained by the following various methods.

A. A method of preparation from the liquid culture of mycelium:

This method comprises cultivation of mycelium of fungi in an appropriate liquid medium to produce glucans and isolation and purification of said glucans through appropriate procedures. The culture medium may be either natural or synthetic.

The mycelium of fungi is inoculated in liquid medium, which is thereafter cultured as usual in a vessel such as shaking flask, jar fermentor, or tank at 25° – 30° C, for 5 to 10 days. A supernatant freed from mycelium by suitable procedure such as filtration or centrifugation is mixed with a suitable amount of an organic solvent miscible with water, such as methanol, ethanol, propanol, and acetone, to obtain glucans as a flocculent precipitate. If necessary, further purification by means of activated carbon, granular activated carbon, bone-char, and ion-exchange resins, and successive treatment with an increasing concentration of a solvent yields white fibrous glucan. Glucan thus obtained is crushed and sieved according to individual use. In some cases, of course, some of the above processes may be omitted. The yield differs from fungus to fungus, but ranges in general between several grams and 10 grams per liter of culture broth.

B. Method of preparation from capsule polysaccharide of fruit body of fungi:

Many fungi, involving mostly Basidiomycetes, are covered with a mucus capsule on their surface. For example, capsule polysaccharides of *Pholiota nameko*, *Pholiota adiposa*, etc., can be easily extracted with cold or warm water. Precipitation and purification to recover glucan from the aqueous extract are carried out according to method (A) mentioned above.

C. Method preparation from fruit body, sclerotium, and mycelium:

Using cold, warm or hot water, or a few percent trichloroacetic acid solution, a few percent alkali solution, glucans can be easily extracted from mycelia. In such cases, it is desirable to homogenate fungi thoroughly.

Precipitation and purification to recover glucan from the extract are carried out according to the above method (A).

The resulting glucans are usually grayish or white and fibrous, tasteless and odorless, and soluble in water, and highly viscous when they are in aqueous solution.

The facts that by the action of an exo-$\beta$-(1 → 3)-glucanase (E. T. Reese et al.: *Can. J. Microbiol.*, 5, 173 (1959); Y. Satomura et al.: *Agr. Biol. Chem.* (Tokyo), 25, 19, (1961)) the glucan utilized in the present invention is easily hydrolysed to yield glucose and gentiobiose, and that after the Smith degradation (J. K. Hamilton, F. Smith: *J. Am. Chem. Soc.*, 78, 5907 (1956)), the same enzymic treatment produces glucose alone, indicate that the glucans have the structure mentioned above.

The methyl, acetyl, carboxymethyl, sulfonyl, phosphoryl and diethyl aminoethyl derivatives may be obtained by conventional methods, and partially hydrolyzed products may be obtained from said glucan by treatment with enzymes, acids and alkalis.

The glucans of the present invention are difficult to prepare in an aqueous solution of higher concentration because of their high viscosity, and therefore, it is desirable to use them in a form of less than 0.5 percent aqueous solution. Furthermore, for the preparation of a medicine, it is necessary to add gradually glucan which is ground as fine as possible into a solvent with violent stirring for complete dispersion, and to continue the stirring until complete dissolution is obtained. In these cases, the use of a high-speed blender is preferable. The above procedures need to be carried out quite carefully, since when any lump is formed it is very difficult to dissolve completely.

The following examples are provided by way of illustration, and are not intended to limit this invention, the scope of which is indicated by the appended claims.

EXAMPLE 1

Humfeld's basal medium (T. Sugihara and H. Humfeld: *Applied Microbiol.*, 2, (3), 170, 1954) was mixed with 3% of glucose, 0.3% of urea, and 1 $\gamma$/ml of thiamine hydrochloride, the volume thereof was made to 1 liter and pH was adjusted to 4.50. Each 100 ml of the resulting medium was poured into a series of 500 ml Sakaguchi flasks. After sterilization at 120° C. for 15 minutes, each flask was inoculated with one loopful of *Schizophyllum commune* (T-189 strain) and cultivated on a reciprocal shaker at 28° C. for 7 days. After completion of fermentation, the culture broth was centrifuged at 8000 r.p.m. for 5 minutes to remove the mycelium, the supernatant thus obtained was decolorized with 0.05% of activated carbon, and filtered under suction with the help of diatomaceous earth. The filtrate was mixed with methanol up to the concentration of 35% to precipitate fibrous glucan, which was washed with portions of aqueous methanol whose concentrations were increased successively and finally with anhydrous methanol to dehydrate, and thereafter the purified fibrous glucan was dried, crushed, and sieved, yielding 8 g of white glucan powder. One gram of the glucan thus obtained were dispersed in 2 liter of physiological saline and after treatment with a high-speed blender for 15 minutes the fully dissolved glucan solution was filtered under suction with the help of diatomaceous earth. Each 20 ml of the filtrate were poured into ampules, the ampules being sealed, and were sterilized at 120° C. for 15 minutes.

EXAMPLE 2

Ascites cells of sarcoma-37 were injected subcutaneously into interscapular region of mice. Each group consisted of ten mice. The amount of tumor cells injected was approximately two million cells per mouse. Injection of saline solution of glucan was made intraperitoneally once daily for 5 days, starting 24 hours after implantation of tumor cells. The mice were autopsied on the 21st day after the implantation and their body weight and tumor weight were estimated. Inhibiton ratio was calculated from average tumor weight of the treated groups as compared with that of the control group. The data obtained are indicated in Table 1.

Table 1

| Dose (mg/kg) | Av. Body weight Change (g) T/C | Av. tumor weight Change (g) T/C | Deaths of treated group | Tumor inhibition ratio (%) |
|---|---|---|---|---|
| 5 | 4.0/8.5 | 0.4/7.6 | 0/10 | 94 |
| 2.5 | 1.5/8.5 | 1.0/7.6 | 0/10 | 87 |
| 1.25 | 2.0/8.5 | 0.8/7.6 | 0/10 | 90 |
| 0.625 | 3.0/8.5 | 2.2/7.6 | 0/10 | 71 |

T = Treated group
C = Control group

A significant inhibition of the tumor growth was observed without accompanying weight loss of mice in the treated group.

EXAMPLE 3

Ascites cells of sarcoma-180 were injected subcutaneously into the right groin of mice. Each group consisted of ten mice. The amount of tumor cells injected was approximately five million cells per mouse. Injection of saline solution of glucan was made intraperitoneally (IP), intravenously (IV), and subcutaneously (SC) once every other day for 20 days, starting 24 hours after implantation of tumor cells. The mice were autopsied on the 31st day ater the implantation and their body weight and tumor weight were estimated. The data obtained are indicated in Table 2.

Table 2

| Dose (mg/kg) | Route | Av. body weight change (g) T/C | Av. tumor weight change (g) T/C | Deaths of treated group | Tumor inhibition ratio (%) |
|---|---|---|---|---|---|
| 0.5 | IP | 0.8/1.8 | 0.5/2.8 | 1/10 | 82 |
| 1 | IP | 1.8/2.0 | 0.9/4.7 | 1/10 | 81 |
| 5 | IP | 0.2/2.0 | 0.5/4.7 | 0/10 | 89 |
| 10 | IP | −0.8/2.0 | 0/4.7 | 0/10 | 100 |
| 1 | SC | 1.1/1.8 | 0.5/2.8 | 0/10 | 82 |
| 1 | IV | 2.0/3.0 | 0.1/2.5 | 0/8 | 96 |
| 5 | IV | 1.3/3.0 | 0/2.5 | 0/8 | 100 |

A significant inhibition of the tumor growth was observed.

EXAMPLE 4

Using Ehrlich carcinoma, an experiment as described in Example 3 was carried out in a similar manner. The data using Ehrlich carcinoma are shown in Table 3.

Table 3

| Dose (mg/kg) | Route | Av. body weight change T/C (g) | Av. tumor weight change T/C (g) | Deaths of treated group | Tumor inhibition ratio (%) |
|---|---|---|---|---|---|
| 1 | IP | 2.1/2.0 | 0.2/4.5 | 0/10 | 96 |
| 5 | IP | 1.8/2.0 | 0.1/4.5 | 0/9 | 98 |

The above data indicate that a significant inhibition in tumor growth was observed without accompanying average weight loss in the treated group.

EXAMPLE 5

Using Yoshida sarcoma in Donryu rats consisting of five animals in each group, an experiment as described in Example 2 was carried out in a similar manner. The data obtained are indicated in Table 4.

Table 4

| Dose (mg/kg) | Av. body weight change (g) T/C | Av. tumor weight change (g) T/C | Deaths of treated group | Tumor inhibition ratio (%) |
|---|---|---|---|---|
| 0.7 | 30/32 | 0.9/3.4 | 0/5 | 74 |
| 0.14 | 22/32 | 2.2/3.4 | 0/5 | 36 |

The above data represent an inhibition of the tumor growth of Yoshida sarcoma without accompanying average weight loss in the treated group.

EXAMPLE 6

An experiment on a combination therapy against sarcoma-180 with the present glucan and simultaneously the known anticancer agents such as Mitomycin C, Endoxan, and Nitromin was carried out in a similar manner as described in Example 3. Injection of saline solution of the glucan was made intraperitoneally into mice. The results are tabulated in Table 5.

Table 5

| Agents | Dose (mg/kg) | Av. body weight change (g) T/C | Av. tumor weight change (g) T/C | Deaths of treated group | Tumor inhibition ratio (%) |
|---|---|---|---|---|---|
| (A) Glucan of the present invention alone | 0.1 | 1.9/2.3 | 2.6/43. | 0/10 | 39 |
| (B) Nitromin alone | 10 | 1.0/2.3 | 3.1/4.3 | 0/10 | 28 |
| (C) Glucan + Nitromin | 0.1, 10 | 1.3/2.3 | 1.3/4.3 | 0/10 | 70 |
| (D) Mitomycin alone | 1.5 | 0/1.8 | 2.1/3.6 | 1/10 | 42 |
| (E) Glucan + Mitomycin C | 0.1, 1.5 | 0.8/1.8 | 0.3/3.6 | 0/10 | 92 |
| (F) Endoxan alone | 80 | 0.9/1.8 | 1.8/3.6 | 0/10 | 50 |
| (G) Glucan + Endoxan | 0.1, 80 | 1.3/1.8 | 0.2/3.6 | 0/10 | 94 |

T = Treated group
C = Control group

EXAMPLE 7

Effects of the derivatives of said glucan on subcutaneously implanted sarcoma-180 of mice are shown in Table 6.

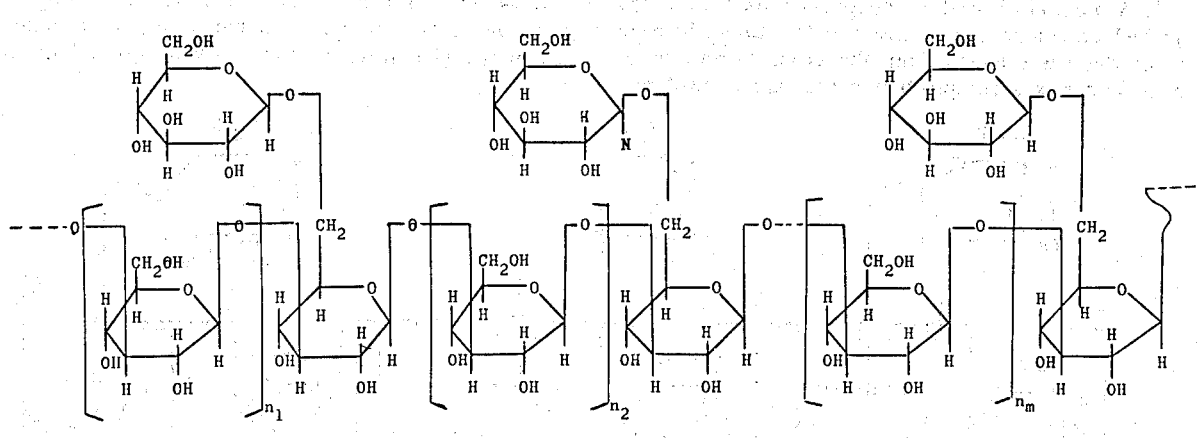

Dose : 5 mg/kg once every 4 days.
Route : ip.

Table 6

| Compound | Av. body weight change (g) T/C | Av. tumor weight change (g) T/C | Mortality at 1 mon. | Tumor inhibition ratio (%) |
|---|---|---|---|---|
| Monophosphor ester | 3.9/1.8 | 0.02/3.07 | 0/10 | 99 |
| Diphosphor ester | 4.0/6.8 | 1.20/6.37 | 0/10 | 81 |
| Methylether | 5.2/6.8 | 1.77/6.37 | 0/10 | 71 |
| Acethylester | 2.5/6.8 | 4.36/6.37 | 0/10 | 32 |
| Carboxymethyl ether | 3.5/1.8 | 2.03/3.07 | 1/10 | 34 |
| Diethylaminoethyl ether | 2.2/6.8 | 0.02/6.37 | 0/10 | 99 |
| Sulfonic acid ester | 3.9/1.8 | 0.88/3.07 | 0/9 | 71 |
| Digestion prod. with enzyme* | −0.2/1.8 | 0.08/3.07 | 0/10 | 99 |

*The digestion product obtained possessed a molecular weight of about half of the molecular weight of original glucan.

What we claim is:

1. A method of treating malignant tumors, selected from the group consisting of Ehrlich carcinoma, Yoshida sarcoma, sarcoma 37 and sarcoma 180, which comprises administering to a tumor-bearing host which is selected from the group consisting of mice and rats a composition containing a substance which is a glucan having the following general structure:

wherein each of $n_1 \ldots n_m$ is the number of linearly B-(1-3)-linked glucose residues, said $n_1 \ldots n_m$ is independently a number from 0 to about 10, in a dose of 0.1 mg to about 10 mg/kg/day.

2. The method of claim 1, wherein the composition is administered to said tumor-bearing mice and rats to provide a dose of a glucan of about 0.1 to 5 mg/kg/day.

3. A composition in dosage unit form adapted for administration to a tumor-bearing host which is selected from the group consisting of mice and rats for use in treating malignant tumors, selected from the group consisting of Ehrlich carcinoma, Yoshida sarcoma, sarcoma 37 and sarcoma 180, comprising, per dosage unit, from about 0.1 to about 10 mg/kg/day of a glucan having the structural formula shown in claim 1 in physiological saline, Ringer's solution or an aqueous glucose solution.

4. A method of treating malignant tumors from sarcoma 180 in tumor-bearing mice and rats which comprises administering to said tumor-bearing mice and rats a composition containing a substance which is methyl ether, acetyl ester, carboxymethyl ether, sulfonic acid ester, monophosphoric acid ester or diphosphoric acid ester or diethylaminoethyl ether of a glucan of formula

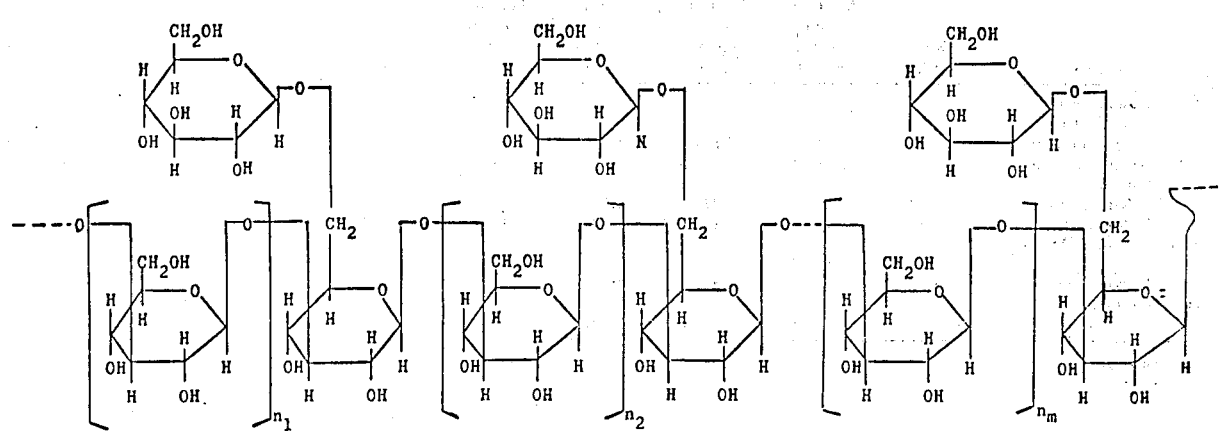

wherein each of $n_1 \ldots n_m$ is the number of linearly B-(1-3)-linked glucose residues, said $n_1 \ldots n_m$ is independently a number from 0 to about 10 in a dose of 0.1 mg/kg/day to about 10 mg/kg/day.

5. A method of treating malignant tumors Sarcoma 180 which comprises administering to a tumor-bearing host which is selected from the group consisting of mice and rats a composition containing a substance which is a glucan having the following general structure:

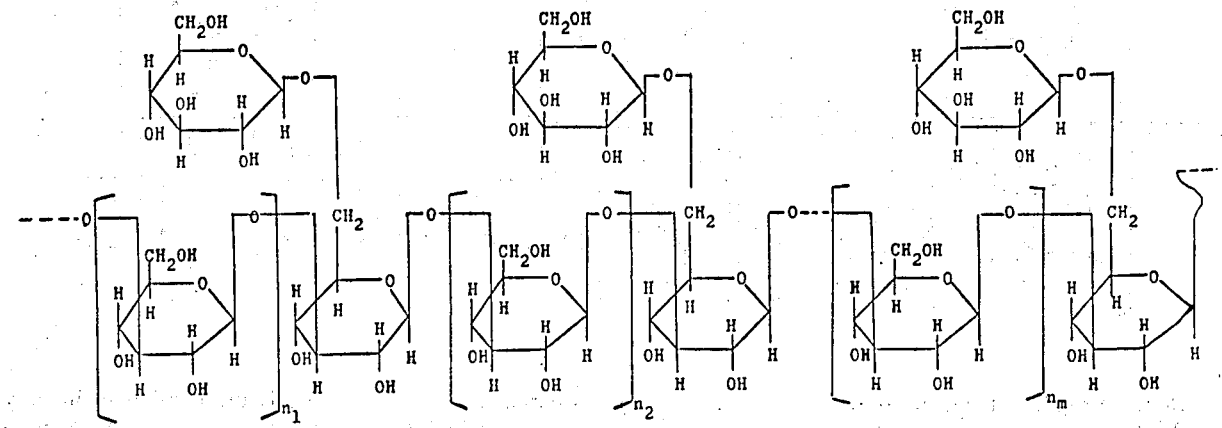

wherein each of $n_1 \ldots n_m$ is the number of linearly B(1-3)-linked glucose residues, said $n_1 \ldots n_m$ is independently a number from 0 to about 10, in a dose of 0.1 mg/kg in admixture with Mytomycin C the later in a dose of 1.5 mg/kg.

6. A method of treating malignant tumors Sarcoma 180 which comprises administering to a tumor-bearing host which is selected from the group consisting of mice and rats a composition containing a substance which is a glucan having the following general structure:

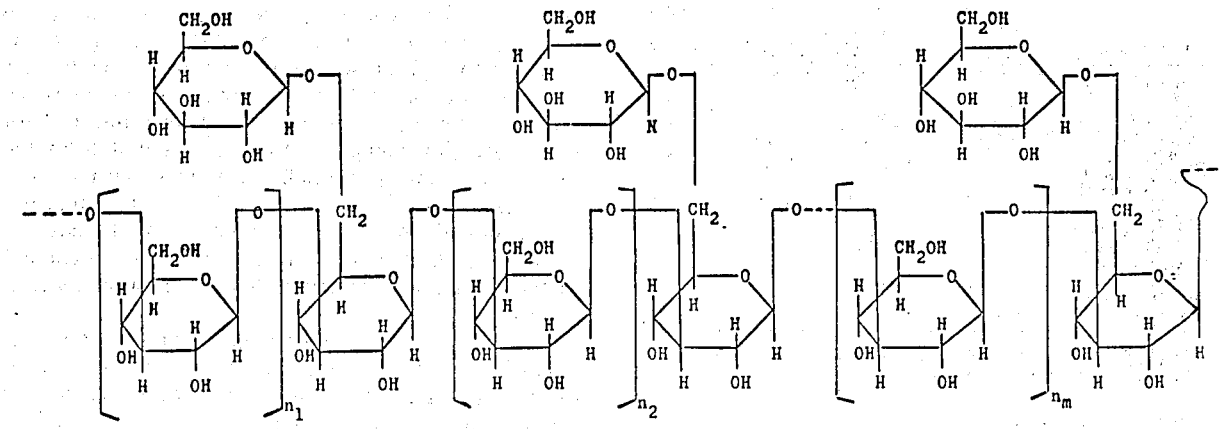

wherein each of $n_1 \ldots n_m$ is the number of linearly B(1-3)-linked glucose residues, said $n_1 \ldots n_m$ is independently a number from 0 to about 10, in a dose of 0.1 mg/kg in admixture with Nitromin, the latter in a dose of 10 mg/kg.

7. A method of treating malignant tumors Sarcoma 180 which comprises administering to a tumor-bearing host which is selected from the group consisting of mice and rats a composition containing a substance which is a glucan having the following general structure:

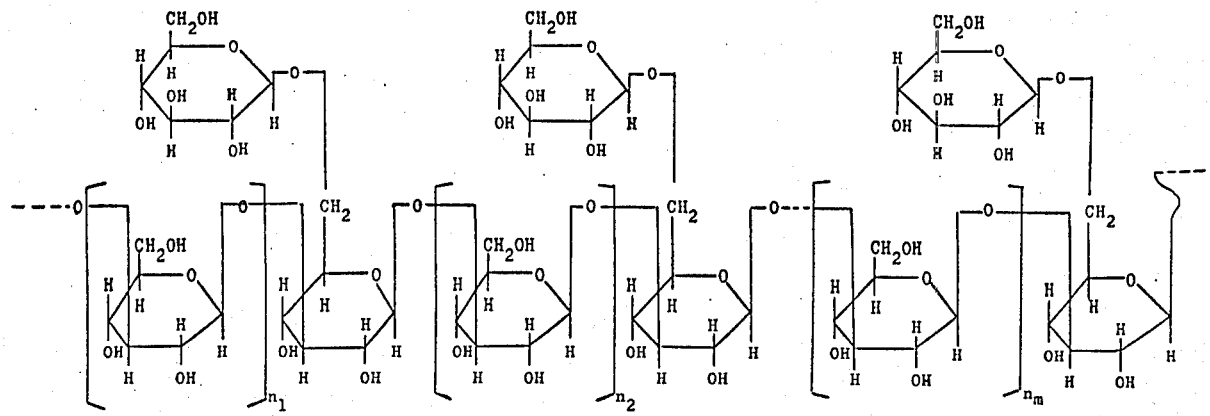

wherein each of $n_1 \ldots n_m$ is the number of linearly B(1-3)-linked glucose residues, said $n_1 \ldots n_m$ is independently a number from 0 to about 10, in a dose of 0.1 mg/kg in admixture with Endoxan, the latter in a dose of 80 mg/kg.

* * * * *